(12) United States Patent
Haralambidis

(10) Patent No.: US 10,098,710 B2
(45) Date of Patent: Oct. 16, 2018

(54) ORTHODONTIC RETENTION COMPONENTS, KIT AND SYSTEM

(71) Applicant: Cosmo Haralambidis, Cranston, RI (US)

(72) Inventor: Cosmo Haralambidis, Cranston, RI (US)

(*) Notice: Subject to any disclaimer, the term of this patent is extended or adjusted under 35 U.S.C. 154(b) by 0 days.

(21) Appl. No.: 15/154,260

(22) Filed: May 13, 2016

(65) Prior Publication Data

US 2017/0035531 A1    Feb. 9, 2017

Related U.S. Application Data

(60) Provisional application No. 62/161,333, filed on May 14, 2015, provisional application No. 62/161,897, (Continued)

(51) Int. Cl.
*A61C 7/08* (2006.01)
*A61C 5/00* (2017.01)
(Continued)

(52) U.S. Cl.
CPC .............. *A61C 7/08* (2013.01); *A61C 5/007* (2013.01); *A61C 7/006* (2013.01); *A61C 7/145* (2013.01); *A61C 7/22* (2013.01); *A61C 7/28* (2013.01)

(58) Field of Classification Search
CPC ........... A61C 7/08; A61C 7/006; A61C 7/145; A61C 7/22; A61C 7/28; A61C 5/007;
(Continued)

(56) References Cited

U.S. PATENT DOCUMENTS 1,307,382 A * 6/1919 Stanton et al. .......... A61C 7/20
                                                                    433/20
3,464,114 A * 9/1969 Brader ..................... A61C 7/12
                                                                    433/10
(Continued)

FOREIGN PATENT DOCUMENTS

EP        1 405 610 A2    4/2004
KR     10-0991835 A      11/2010
(Continued)

OTHER PUBLICATIONS

International Search Report and Written Opinion received for Application No. PCT/US2016/032390, dated Sep. 8, 2016, 8 pages.
Artun et al., "A 3-year follow-up study of various types of orthodontic canine-to-canine retainers", European Journal of Orthodontics 19 (1997) 501-509, Downloaded from http://ejo.oxfordjournals.org/ at SCD Universit? Paris 5 on Jan. 30, 2012, 8 pages.
(Continued)

*Primary Examiner* — Nicholas Lucchesi
*Assistant Examiner* — Shannel Wright
(74) *Attorney, Agent, or Firm* — Patent GC LLC

(57) ABSTRACT

An orthodontic retention system includes a fixed component that remains on teeth and a component that attaches to this fixed component. The fixed component and the component have mating or interlocking parts. The component that mates with the fixed component can be removable. The component that mates with the fixed component can be adjustable. The retention system also can include magnetic retention components to retain the removable component with respect to one or more teeth. The retention system also can include an element that replaces as tooth.

6 Claims, 19 Drawing Sheets

Related U.S. Application Data filed on May 15, 2015, provisional application No. 62/186,588, filed on Jun. 30, 2015.

(51) Int. Cl.
- *A61C 7/14* (2006.01)
- *A61C 7/22* (2006.01)
- *A61C 7/00* (2006.01)
- *A61C 7/28* (2006.01)

(58) Field of Classification Search
CPC .... A61C 5/30; A61C 5/70; A61C 5/73; A61C 13/225
USPC ......................................................... 433/18
See application file for complete search history.

(56) References Cited

U.S. PATENT DOCUMENTS

| | | |
|---|---|---|
| 3,950,851 A | 4/1976 | Bergersen |
| 3,994,068 A | 11/1976 | Goshgarian |
| 4,144,642 A | 3/1979 | Wallshein |
| 4,302,187 A * | 11/1981 | Yoon ................ A61C 13/225 433/172 |
| 4,413,978 A | 11/1983 | Kurz |
| 4,431,417 A * | 2/1984 | Weissman .......... A61C 13/2653 433/182 |
| 4,433,960 A * | 2/1984 | Garito .................. A61C 7/00 433/180 |
| 4,455,137 A | 6/1984 | Diamond |
| 4,516,938 A * | 5/1985 | Hall ..................... A61C 5/00 433/180 |
| 4,527,975 A * | 7/1985 | Ghafari ................ A61C 7/00 433/8 |
| 4,533,320 A * | 8/1985 | Piekarsky ............. A61C 7/00 433/10 |
| 4,609,350 A * | 9/1986 | Krause ................. A61C 5/00 433/215 |
| 4,725,230 A | 2/1988 | Harima |
| 4,871,310 A * | 10/1989 | Vardimon ............ A61C 7/006 433/18 |
| 4,886,451 A * | 12/1989 | Cetlin .................. A61C 7/282 433/7 |
| 5,096,416 A | 3/1992 | Hulsink |
| 5,123,843 A | 6/1992 | Van der Zel et al. |
| 5,145,364 A | 9/1992 | Martz et al. |
| 5,184,955 A * | 2/1993 | Baer .................... A61C 5/007 433/215 |
| 5,312,247 A * | 5/1994 | Sachdeva ............. A61C 7/10 433/18 |
| 5,356,289 A | 10/1994 | Watanabe |
| 5,536,169 A | 7/1996 | Yousefian |
| 5,580,243 A | 12/1996 | Bloore |
| 5,607,300 A | 3/1997 | Tepper |
| 5,785,526 A * | 7/1998 | Barnes .................. A61C 5/77 433/178 |
| 5,788,493 A | 8/1998 | Tanaka et al. |
| 5,820,369 A * | 10/1998 | Kvarnstrom ......... A61B 17/663 433/173 |
| 5,829,975 A | 11/1998 | Gold |
| 5,846,640 A * | 12/1998 | Vallittu ................ A61K 6/083 427/195 |
| 6,062,855 A * | 5/2000 | Karlin ................. A61C 7/006 433/20 |
| 6,302,688 B1 | 10/2001 | Jordan et al. |
| 6,358,255 B1 * | 3/2002 | Testa .................. A61B 17/663 433/7 |
| 6,540,515 B1 | 4/2003 | Tanaka |
| 6,582,226 B2 | 6/2003 | Jordan et al. |
| 6,663,385 B2 | 12/2003 | Tepper |
| 7,014,460 B2 | 3/2006 | Lai et al. |
| 7,121,825 B2 * | 10/2006 | Chishti ................. A61C 7/00 433/6 |
| 7,175,428 B2 | 2/2007 | Nicholson |
| 7,234,934 B2 * | 6/2007 | Rosenberg ............ A61C 7/12 433/6 |
| 7,252,505 B2 | 8/2007 | Lai |
| 7,300,279 B2 | 11/2007 | Amundsen |
| 7,722,354 B1 | 5/2010 | Dumas |
| 7,780,441 B2 | 8/2010 | Amundsen |
| 7,819,661 B2 * | 10/2010 | Nadav .................. A61C 7/006 433/18 |
| 7,854,610 B2 | 12/2010 | Dellinger et al. |
| D638,129 S | 5/2011 | Inman |
| 7,997,898 B2 | 8/2011 | Ortiz et al. |
| 8,118,592 B2 | 2/2012 | Tortorici |
| 8,147,244 B2 | 4/2012 | Dellinger et al. |
| 8,356,993 B1 * | 1/2013 | Marston ............... A61C 7/08 433/24 |
| 8,459,988 B2 | 6/2013 | Dumas |
| 8,523,564 B2 | 9/2013 | Dellinger et al. |
| 8,568,139 B2 | 10/2013 | Roncone |
| 8,827,696 B1 | 9/2014 | Sandwick |
| 9,498,302 B1 * | 11/2016 | Patel .................... A61C 7/006 |
| 2001/0036615 A1 | 11/2001 | Binder |
| 2003/0104335 A1 * | 6/2003 | Chung ................. A61C 7/12 433/18 |
| 2003/0124478 A1 * | 7/2003 | Amundsen ........... A61C 5/007 433/18 |
| 2004/0067463 A1 * | 4/2004 | Rosenberg ............ A61C 7/12 433/6 |
| 2005/0277084 A1 | 12/2005 | Cinader et al. |
| 2006/0172262 A1 * | 8/2006 | Bruce .................. A45D 44/22 433/229 |
| 2006/0199137 A1 * | 9/2006 | Abels .................. A61C 7/12 433/11 |
| 2007/0231768 A1 | 10/2007 | Hutchinson |
| 2008/0057460 A1 * | 3/2008 | Hicks .................. A61C 5/007 433/20 |
| 2009/0047614 A1 * | 2/2009 | Fathianathan ........ A61C 7/08 433/6 |
| 2009/0061379 A1 * | 3/2009 | Yamamoto .......... A61C 7/00 433/24 |
| 2009/0061380 A1 * | 3/2009 | Yamamoto .......... A61C 7/00 433/24 |
| 2009/0148804 A1 * | 6/2009 | Marcus ................ A61C 5/007 433/7 |
| 2009/0162806 A1 * | 6/2009 | Wickizer .............. A61C 7/00 433/8 |
| 2010/0015565 A1 * | 1/2010 | Carrillo Gonzalez ... A61C 5/00 433/7 |
| 2010/0136497 A1 | 6/2010 | Guray |
| 2010/0183997 A1 * | 7/2010 | Darendeliler ........ A61C 7/006 433/6 |
| 2011/0027743 A1 * | 2/2011 | Cinader, Jr. .......... A61C 7/10 433/11 |
| 2011/0129786 A1 * | 6/2011 | Chun .................... A61C 7/08 433/19 |
| 2012/0052458 A1 | 3/2012 | Harman |
| 2012/0115100 A1 * | 5/2012 | Borri .................... A61C 7/22 433/18 |
| 2012/0220986 A1 * | 8/2012 | Wolff .................. A61M 31/002 604/892.1 |
| 2012/0225397 A1 * | 9/2012 | Haikel .................. A61C 7/02 433/3 |
| 2012/0225398 A1 * | 9/2012 | Fallah .................. A61C 7/12 433/8 |
| 2013/0052603 A1 * | 2/2013 | Ahn .................... A61C 7/145 433/7 |
| 2013/0122445 A1 | 5/2013 | Marston |
| 2013/0230820 A1 * | 9/2013 | Carrillo Gonzalez ... A61C 5/00 433/7 |
| 2014/0008583 A1 | 1/2014 | Wang et al. |
| 2014/0123782 A1 | 5/2014 | Kittleson et al. |
| 2014/0272757 A1 * | 9/2014 | Chishti ................ A61C 7/125 433/18 |
| 2014/0302448 A1 * | 10/2014 | Cassalia .............. A61C 7/28 433/9 |
| 2014/0363779 A1 | 12/2014 | Kopelman |
| 2015/0157421 A1 * | 6/2015 | Martz .................. A61C 7/08 433/6 |

(56) References Cited

U.S. PATENT DOCUMENTS

| | | | |
|---|---|---|---|
| 2015/0257856 A1* | 9/2015 | Martz | A61C 7/14 |
| | | | 433/6 |
| 2015/0327957 A1 | 11/2015 | Faust et al. | |
| 2015/0335398 A1* | 11/2015 | Rosenthall | A61C 7/08 |
| | | | 433/6 |
| 2016/0058527 A1 | 3/2016 | Schumacher | |
| 2016/0081767 A1 | 3/2016 | Metcalf et al. | |
| 2016/0120620 A1 | 5/2016 | Tairaku | |
| 2016/0184067 A1* | 6/2016 | Parker | A61C 7/12 |
| | | | 433/18 |
| 2016/0206403 A1* | 7/2016 | Ouellette | A61C 7/146 |
| 2016/0206405 A1* | 7/2016 | Reybrouck | A61C 7/12 |
| 2016/0296303 A1* | 10/2016 | Parker | A61C 8/0096 |
| 2016/0331950 A1* | 11/2016 | Su | A61C 7/08 |
| 2016/0361141 A1 | 12/2016 | Tong et al. | |

FOREIGN PATENT DOCUMENTS

| | | |
|---|---|---|
| KR | 10-2013-0125132 A | 11/2013 |
| WO | 2006/127511 A2 | 11/2006 |
| WO | 2014/008583 A1 | 1/2014 |
| WO | 2014/144886 A1 | 9/2014 |
| WO | 2016183457 A1 | 11/2016 |

OTHER PUBLICATIONS

Spadafora et al., "Hygiene status associated with different types of bonded, orthodontic canine-to-canine retainers", A clinical trial, dated Jan. 28, 1986, pp. 89-94.

* cited by examiner

ORTHODONTIC RETENTION COMPONENTS, KIT AND SYSTEM

CROSS-REFERENCE TO RELATED APPLICATIONS

This application is a nonprovisional application of the following U.S. provisional patent applications, all of which are hereby incorporated by reference:

a. U.S. Provisional Patent Application Ser. No. 62/161,333, filed May 14, 2015, entitled Orthodontic Retention Components, Kit and System, by Cosmo Haralambidis;

b. U.S. Provisional Patent Application Ser. No. 62/161,897, filed May 15, 2015, entitled Orthodontic Retention Components, Kit and System, by Cosmo Haralambidis; and c. U.S. Provisional Patent Application Ser. No. 62/186,588, filed Jun. 30, 2015, entitled Orthodontic Retention Components, Kit and System, by Cosmo Haralambidis.

BACKGROUND

Orthodontic treatment generally involves attaching appliances to teeth, and then adjusting those appliances to move the teeth into desired positions and orientations. Such appliances typically include braces attached to the teeth, and wires connected to the braces. Adjustments are made to the wires, which cause forces to be applied to the teeth, which in turn move the teeth. In some cases, an individual may have replacement teeth, which may be permanent or temporary.

After the desired positions and orientations of the teeth have been achieved, in most instances, additional appliances, called retainers or retention systems, are used to retain the teeth in the corrected positions and orientations. Occasionally, such retainers or retention systems have a secondary function of moving the teeth. Currently used types of retainers include plastic, thermo-formic, removable retainers, which are formed to the shape of an individual's mouth and include wires to retain the teeth in the desired positions and orientations. Other retainers include brackets cemented to the teeth, with fixed wires attached to the brackets.

SUMMARY

This Summary introduces selected concepts in simplified form which are described further below in the Detailed Description. This Summary is intended neither to identify essential features, nor to limit the scope, of the claimed subject matter.

A removable orthodontic retention system includes a bracket that remains on teeth, and thus can be referred to as a "fixed" component, and a removable component that attaches to, yet is easily removable from, this bracket. Thus the bracket and the removable component have mating or interlocking parts. The removable component can be adjustable. The retention system also can include magnetic retention components to retain the removable component with respect to one or more teeth.

In one aspect, the orthodontic retention system includes an adjustable component that connects between two fixed components that attach to teeth. In another aspect, the orthodontic retention system includes a removable component that attaches to, yet is easily removable from, a fixed component. In another aspect, the orthodontic retention system includes magnetic components and mechanical retentive components. In another aspect, the orthodontic retention system includes a cosmetic tooth. In another aspect, a kit for an orthodontic retention system includes a plurality of brackets and a removable component for connection to the brackets. In another aspect, a bracket for an orthodontic retention system includes an opening for receiving a mating mechanical interconnection from a projection on a removable component of the retentive system. In another aspect, an adjustable component for an orthodontic retention system is provided. In another aspect, the retention system can include adjustable parts, such as orthodontic wires, that can be adjusted to effect movement or realignment of teeth. Such parts can be removable to allow the retention system to be used as either a retention system or an orthodontic treatment system.

Such a removable orthodontic retention system can maintain the position and orientation of teeth and not interfere with bite, while allowing for cleaning of teeth, and simplifying replacing missing teeth and repairing damaged teeth. The retention system can be initially configured and inserted by a provider, and then can be removed and re-inserted by a provider or a patient.

In the following description, reference is made to the accompanying drawings which form a part hereof, and in which are shown, by way of illustration, specific example implementations of this technique. It is understood that other embodiments may be utilized and structural changes may be made without departing from the scope of the disclosure.

DETAILED DESCRIPTION

Figure 1:
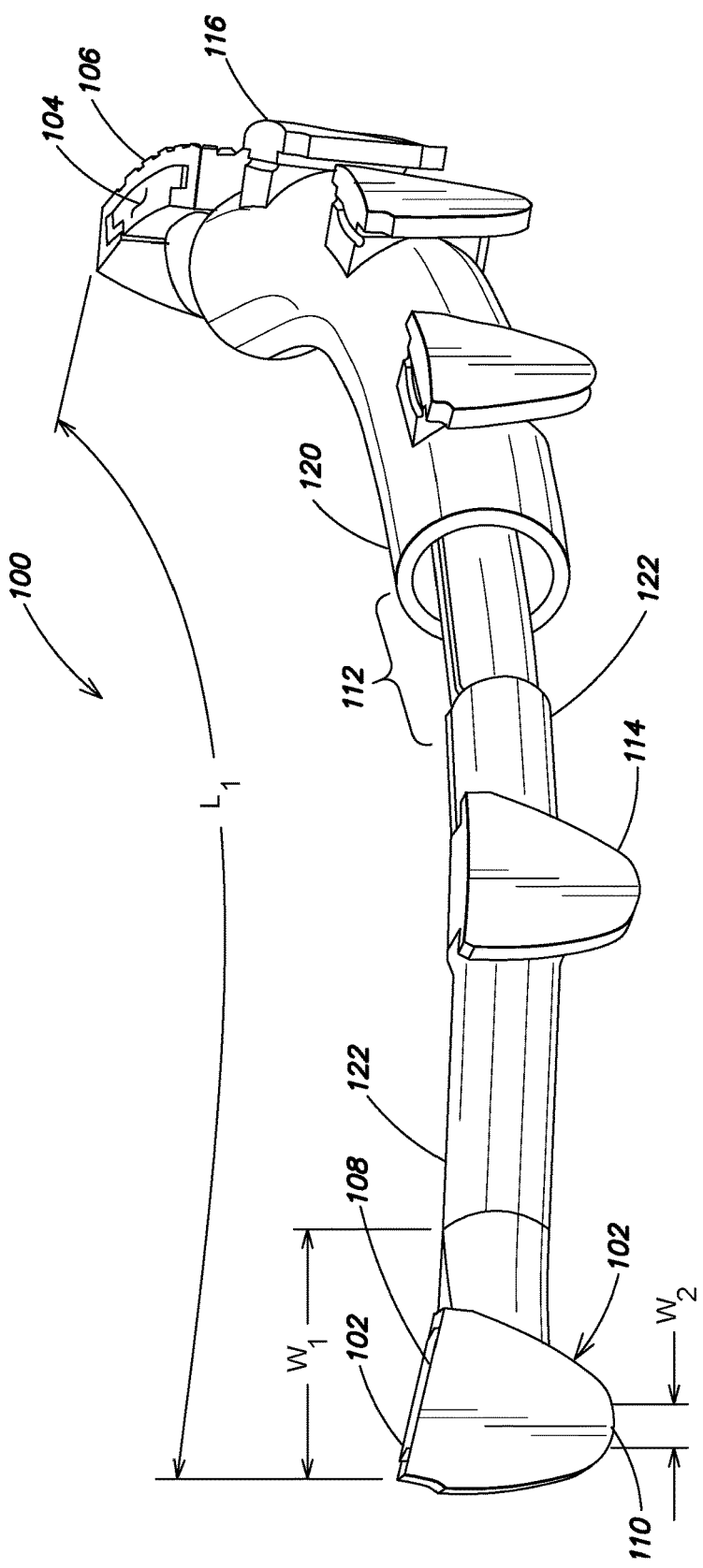
FIG. 1 is a perspective front view of an example embodiment of a removable component of an orthodontic retention system.

Referring now to FIG. 1, a perspective front view of an example embodiment of a removable component of an orthodontic retention system will now be described.

In FIG. 1, the example embodiment is configured for use for a mandibular lingual arch. Other embodiments can be configured for a maxillary arch. The orthodontic retention system includes a removable component 100. The removable component 100 includes a first projection 102 and a second projection 104. Additional example embodiments of such projections are described in more detail below. Generally, the first projection 102 has a shape that mates with a socket of a first fixed component (not shown) attached to a first tooth. The second projection 104 has a shape that mates with a socket of a second fixed component 106 attached to a second tooth. The first and second fixed components, examples of which are described in more detail below, are configured to be attached to teeth at opposite ends of a span of teeth for which the orthodontic retention system is being used, such as the canines on the mandibular lingual arch. The shape of the fixed component is based on the tooth surface to which it will be attached so as to conform to the anatomy of the tooth.

Additional projections, e.g., 114 and 116, also can be provided, which in turn mate with sockets of other fixed components (not shown) attached to other teeth along the arch such as the incisors.

In the example shown in FIG. 1, the first and second projections 102 and 104 are tapered in shape. For example, the projection can gradually reduce in width from a top edge 108 and a bottom edge 110 as shown at W1 and W2. The projection can gradually reduce in thickness from the top edge 108 and the bottom edge 110. The projection can gradually reduce in both width and thickness. Such a gradual reduction can be nonuniform, and can include one or more shapes designed to provide a snapping or interlocking function.

In the example shown in FIG. 1, the removable component 100 also has a curved member 112, have a curved shape designed to correspond to the shape of the arch with which the orthodontic retention system will be used. The curved member 112 can have a length L1, between the first projection 102 and the second projection 104, which is adjustable.

In one example embodiment, as shown in FIG. 1, the removable component 100 is adjustable by comprising a base component 120 and a telescoping component 122 that can be moved with respect to the base component 120 along the curve shown at L1 to adjust the length L1. In FIG. 1, the base component 120 is hollow, and tubular, and the telescoping component is rod shaped. Other telescoping structures can be used. Alternatively, the removable component 100 can be constructed with a fixed length. As described in more detail below, the relative position of the telescoping component 122 with respect to the base component 120 can be adjusted, and optionally fixed after adjustment, using a mechanical structure.

Figure 2:
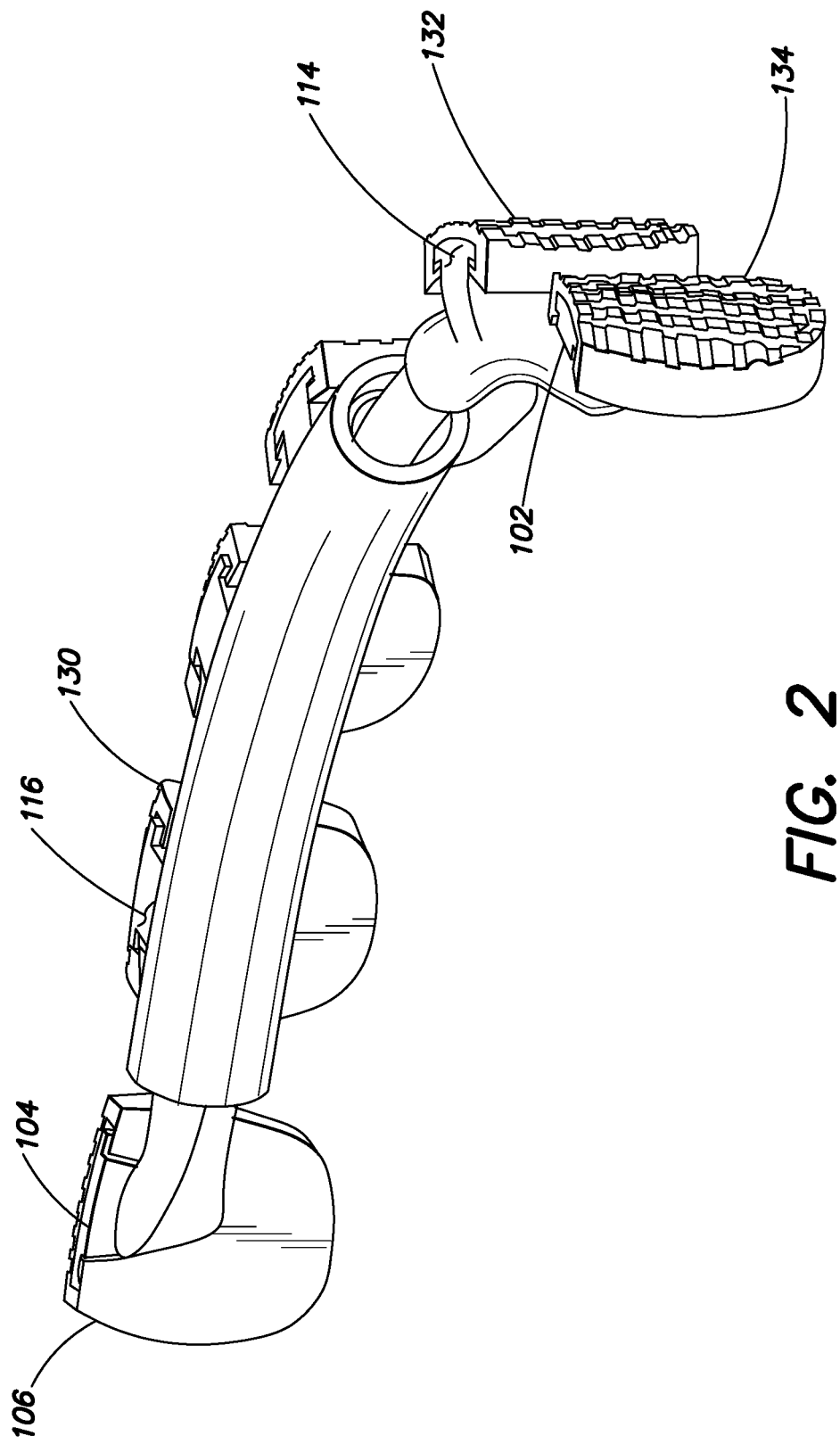
FIG. 2 is a perspective back view of an example embodiment of a removable component of an orthodontic retention system.

Referring now to FIG. 2, a perspective back view of the example embodiment of a removable component of an orthodontic retention system will now be described. In FIG. 2., each of the projections, e.g., 102, 104, 114, 116, on the removable component are shown in a mating configuration with fixed components, e.g., 106, 130, 132 and 134.

Figure 3:
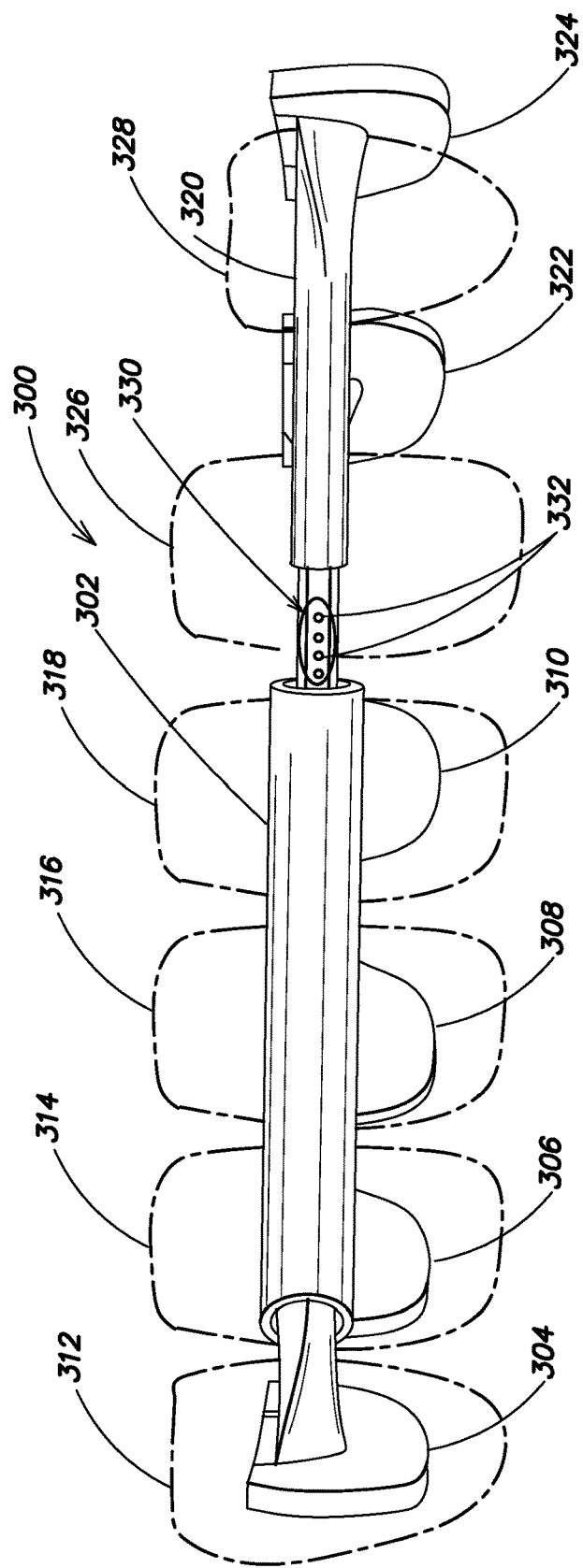
FIG. 3 is a back plan view of an example embodiment of a removable component of an orthodontic retention system.

Referring now to FIG. 3, a back plan view of an example embodiment of a removable component of an orthodontic retention system will now be described. In FIG. 3, the orthodontic retention system is shown with respect to an installation for a mandibular lingual arch. In this example, the removable component 300 is adjustable, and is illustrated as not adjusted to match the arch. In particular, the base component 302 is configured with projection 304, 306, 308 and 310 which are spaced to match, respectively, left canine 312, a left lateral incisor 314, a left central incisor 316 and right central incisor 318. The telescoping component 320 is to be adjusted such that its projections 322 and 324 are arranged to match, respectively, right lateral incisor 326 and right canine 328.

Also shown in FIG. 3 is one example of a mechanical structure, namely a cam system 330, which provides stepwise adjustments of the telescoping component 320 with respect to the base component 302. In this example, the cam system 330 includes a plurality of spaced projections 332 which interlock with a corresponding structure (not shown in FIG. 3) in the base component 302. In particular, an example spacing to be used is a one (1) millimeter (mm) spacing of each projection. Other adjustable structures, such as a saw or tooth shaped structure, a screw-type or rotatable design, or a piston design, for example, can be used.

Figure 4:
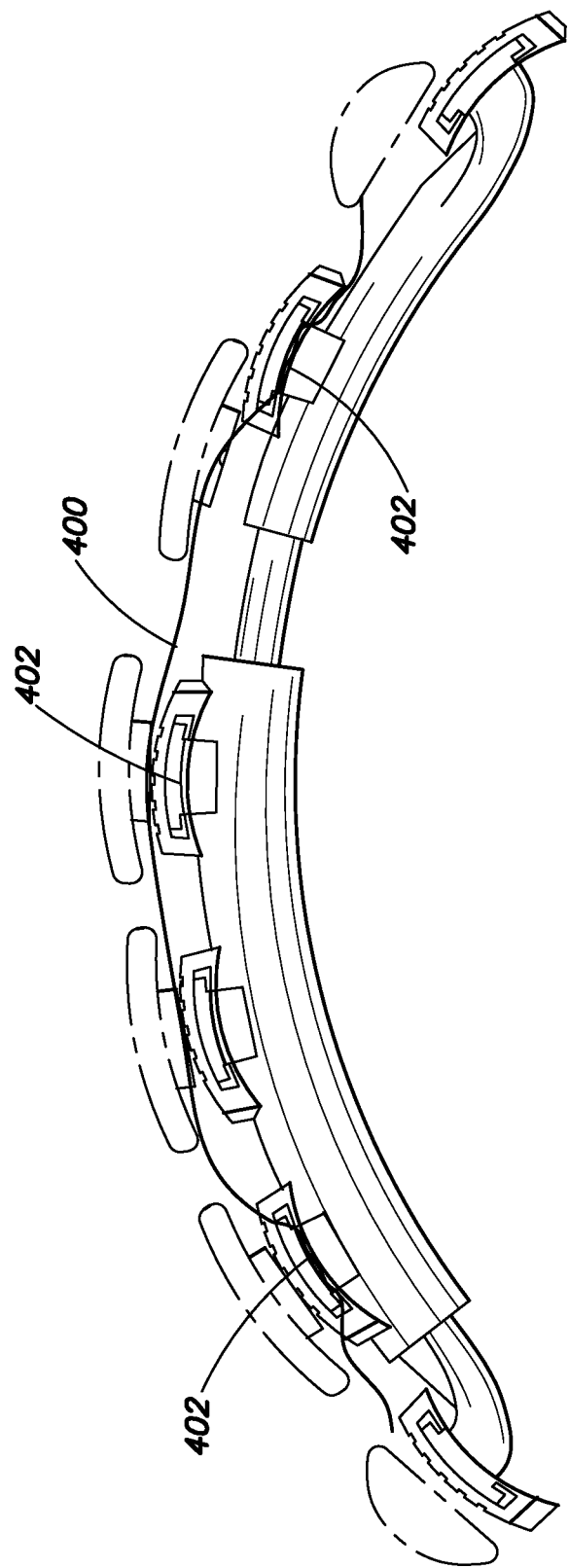
FIG. 4 is a top plan view of an example embodiment of a removable component of an orthodontic retention system.

FIG. 4 is a top plan view of an example embodiment of an adjustable removable component of an orthodontic retention system. In addition to the components shown in FIG. 3, FIG. 4 illustrates an optional orthodontic wire 400. The orthodontic wire can be inserted in horizontal slots 402 along the length of a portion of the retention system. Such slots can be formed, for example, in the tops of the brackets or in the tops of the projections along the removable component. In such an embodiment, the retention system can also be used to effect orthodontic treatment by manipulating the orthodontic wire to cause a force to be applied to teeth. Such an embodiment is particularly useful for patients who have suffered anterior (front) tooth relapse. The relapse can be treated and the device is then converted back to a stable retention system. As an example, such a slot can have a size of 0.018 inches to accept orthodontic wires of about 0.016 inches.

Figure 5:
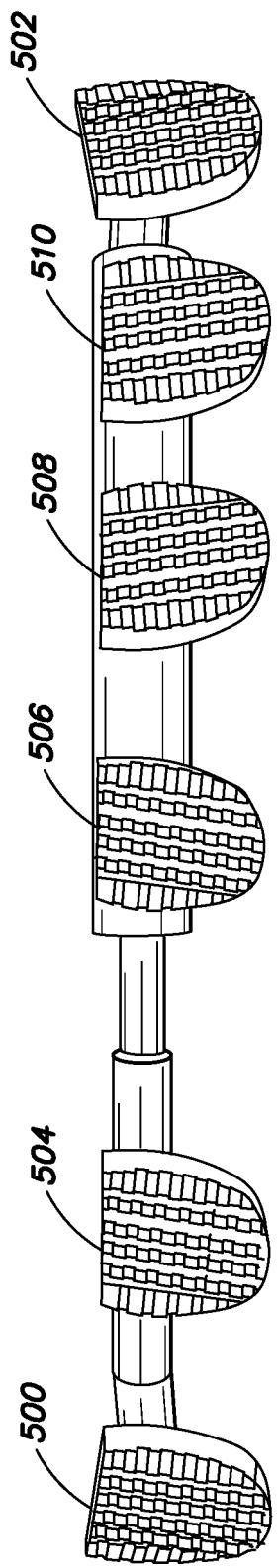
FIG. 5 is a front plan view of an example embodiment of a removable component of an orthodontic retention system.

FIG. 5 is a front plan view of an example embodiment of a removable component of an orthodontic retention system. In this example, the first and second projections 500 and 502 are shown attached to brackets that attach to the teeth. Projections 504, 506, 508 and 510, for the incisors for example, are designed in the shape of the combined projection and bracket, and are design to mate with a substance formed on the back of the teeth. In particular, on the back face of the tooth is placed a material forming a base, with the base having a face opposite the back face of the tooth and having a surface. The material of the base includes at least one of a magnetic material or ferrometallic material. Then, the corresponding internal projection (e.g., 504, 506, 508, 510) has at least one of a magnetic material or ferrometallic material such that magnetic attraction occurs between the projection and the base formed on the back of the tooth. The base can be formed, for example, of a paint or enamel substance, which may be called a magnetic primer, which is applied to the back of the tooth. The base can be formed by a bracket with a smooth surface that is affixed (e.g., by orthodontic cement) to the back of the tooth.

To provide such a magnetic component, a small magnet of neodymium iron boron, SmCo, Alnico, or any other magnetic material, with a biocompatible coatings or platings, such as Parylene or Titanium, designed for medical applications, such as those available from BJA Magnetics, may be used. As another example, a dental bonding agent or dental primer or similar material for intra-oral use that can be applied to a tooth surface, such as those available from Reliance Orthodontic Products, Inc., can be embedded with particles of magnetic or ferrometallic material such as cobalt chromium or ingredients such as found in readily available iron pills for human consumption, such as carbonyl iron used in a range of levels. For example, a 15 mg carbonyl iron tablet, crushed into a powder, can be mixed in a ratio of two parts liquid primer or bonding agent to one part iron and used on either a tooth or the retainer. As another example, a 50 mg carbonyl iron tablet, crushed into a powder can provide a greater attractive force and reduce the amount of iron needed in the mixture with the liquid primer or bonding agent. Other tablets, such as in the range of 10 mg to 200 mg carbonyl iron tablets can be used. Any other combination or mixture of iron supplement ingredients, or other biocompatible ferrometallic, ferrous or magnetic materials, with a biocompatible bonding agent or primer or other material that can be applied to teeth also can be used.

The use of such magnetic components for some of the teeth simplifies insertion and removal of the retainer due to few mechanical retentive elements being used. Thus a blended retentive system can use mechanical retentive components on primary retentive segments and magnetic retentive components on secondary retentive segments. The magnetic retention primarily retains the position of teeth, and secondarily maintains the appliance in a specific plane of space.

Figure 6:
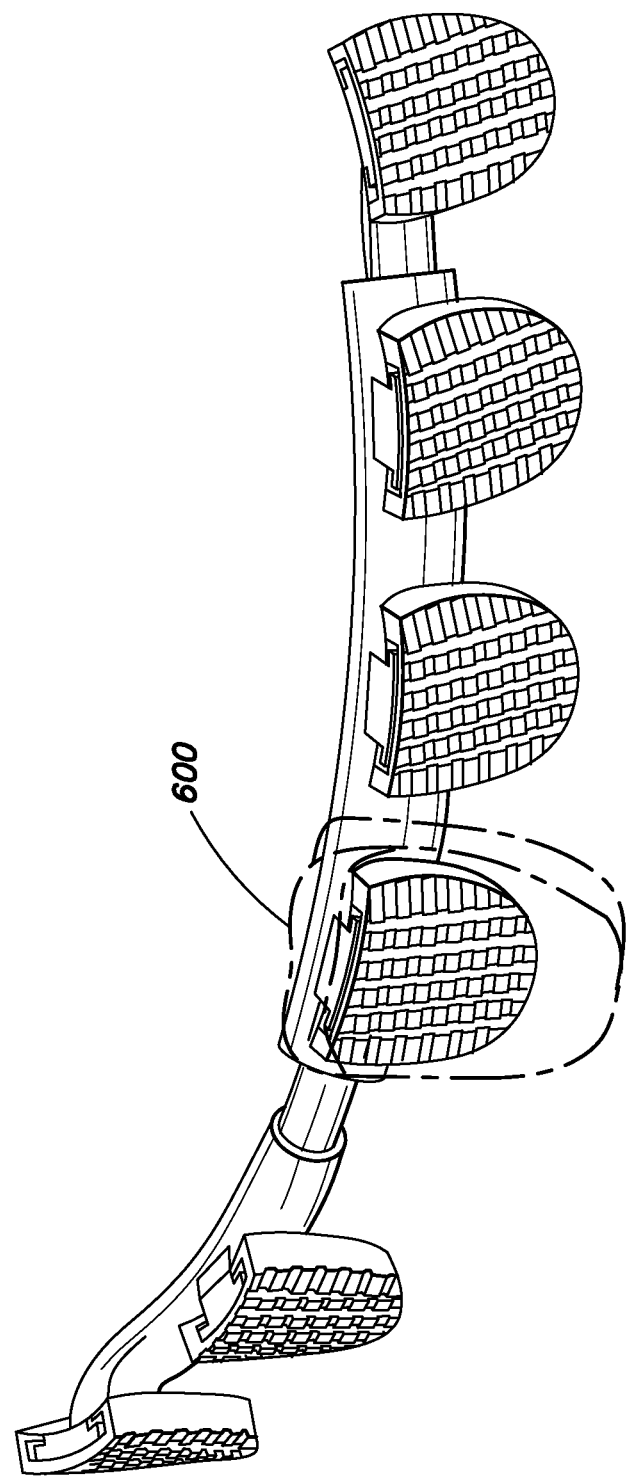
FIG. 6 is a front perspective view of an example embodiment of a removable component of an orthodontic retention system.

FIG. 6 is a front perspective view of an example embodiment of a removable component of an orthodontic retention system. In this example, an element 600 is placed on the removable component and spaced between the first and second projections. This element has a shape of a tooth and fits between teeth when the removable component is installed. In this configuration, this removable component supports a temporary replacement tooth for the patient. A wide variety of prosthodontic components can be added to the removable component. Using a removable component as described herein with a prosthodontic component can be one application of such a device as a removable prosthodontic appliance, which can be particularly useful in a retentive, stabilization phase of dental treatment. In one embodiment, a bracket can be provided on the removable component, which in turn can be attached to any prosthodontic part that may be prepared for a patient.

The removable component can have any combination of magnetic components and/or temporary replacement teeth along the removable component between the first and second projections which provide the primary attachment of the retention system through the removable component to the teeth.

Figure 7:
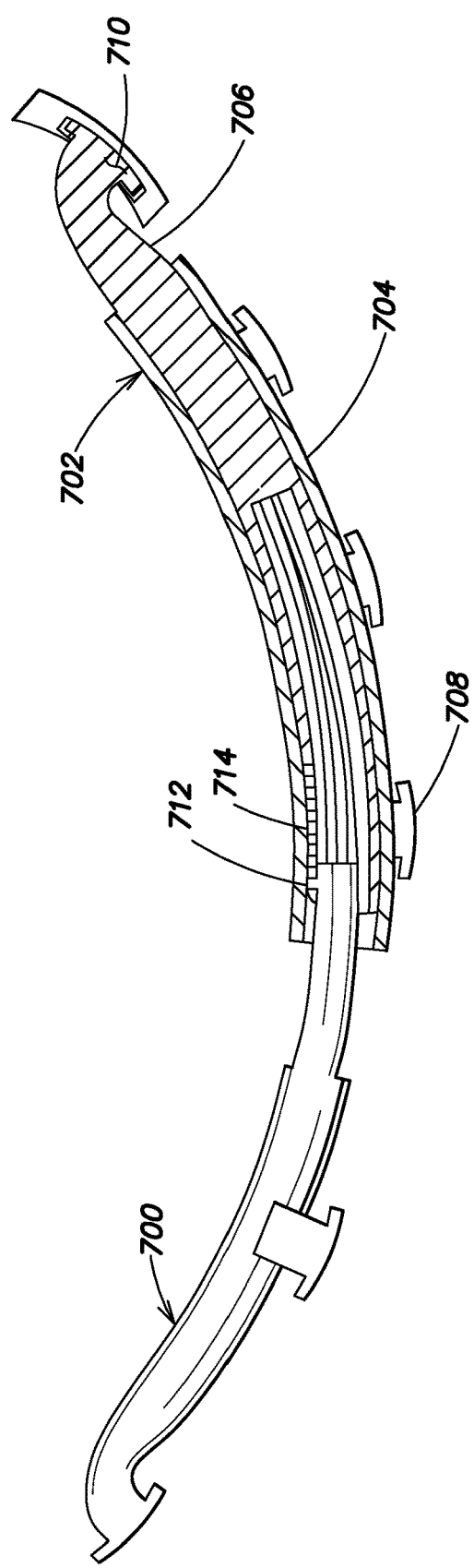
FIG. 7 is a cross-sectional, top plan view of an example embodiment of a removable component of an orthodontic retention system.

FIG. 7 is a cross-sectional, top plan view of an example embodiment of a removable component of an orthodontic retention system.

In FIG. 7, a telescoping component 700 inserts into a base component 702, which is illustrated as hollow and tubular. The telescoping and base components are formed to support projections that are associated with endpoint teeth at the ends of the retention system. The base component further can be manufactured in two parts, with a first component 704 being formed to support projections, e.g. 708, that are associated with intermediate teeth along the retention system, whereas a second component 706 supports a projection 710 for an endpoint tooth. The use of the two components 704 and 706 allows for their separate manufacture (to include different types of projections, magnetic components and/or replacement teeth) and additional adjustability. The two components 704 and 706 can be adjusted into position and crimped together, for example, to maintain their relative position after adjustment.

The telescoping component 700 and base component 702 also can include mechanical structures allowing for relative positional adjustment. For example, a projection 712 can be provided on the telescoping component 700. The projection 712 interlocks with a corresponding structure 714 on the base component. After adjustment, the two components 700 and 702 can be adjusted into position and crimped together, for example, to maintain their relative position.

Figure 8:
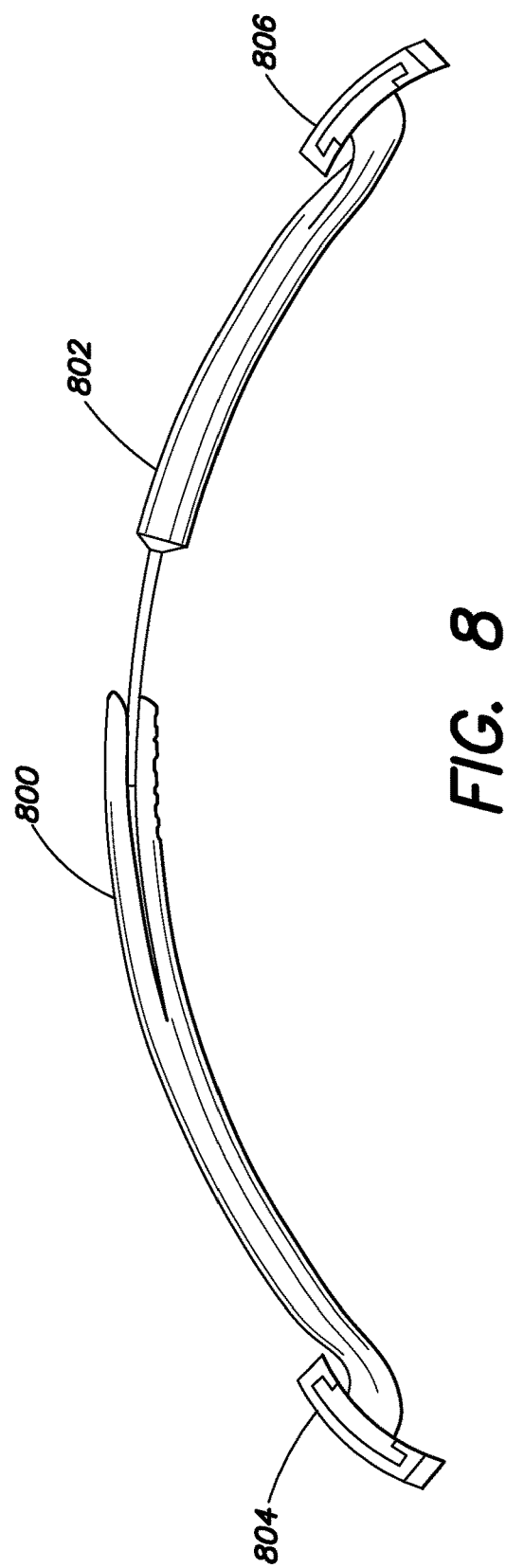
FIG. 8 is a cross-sectional, top plan view of an example embodiment of a removable component of an orthodontic retention system.

FIG. 8 is a cross-sectional, top plan view of an example embodiment of a removable component of an orthodontic retention system. In FIG. 8, a similar structure is shown, with a base component 800 and telescoping component 802. In this example, the retention system only has endpoint projections 804 and 806. Other projections can be added after measurement and adjustment of the combined components 800 and 802.

Figure 9:
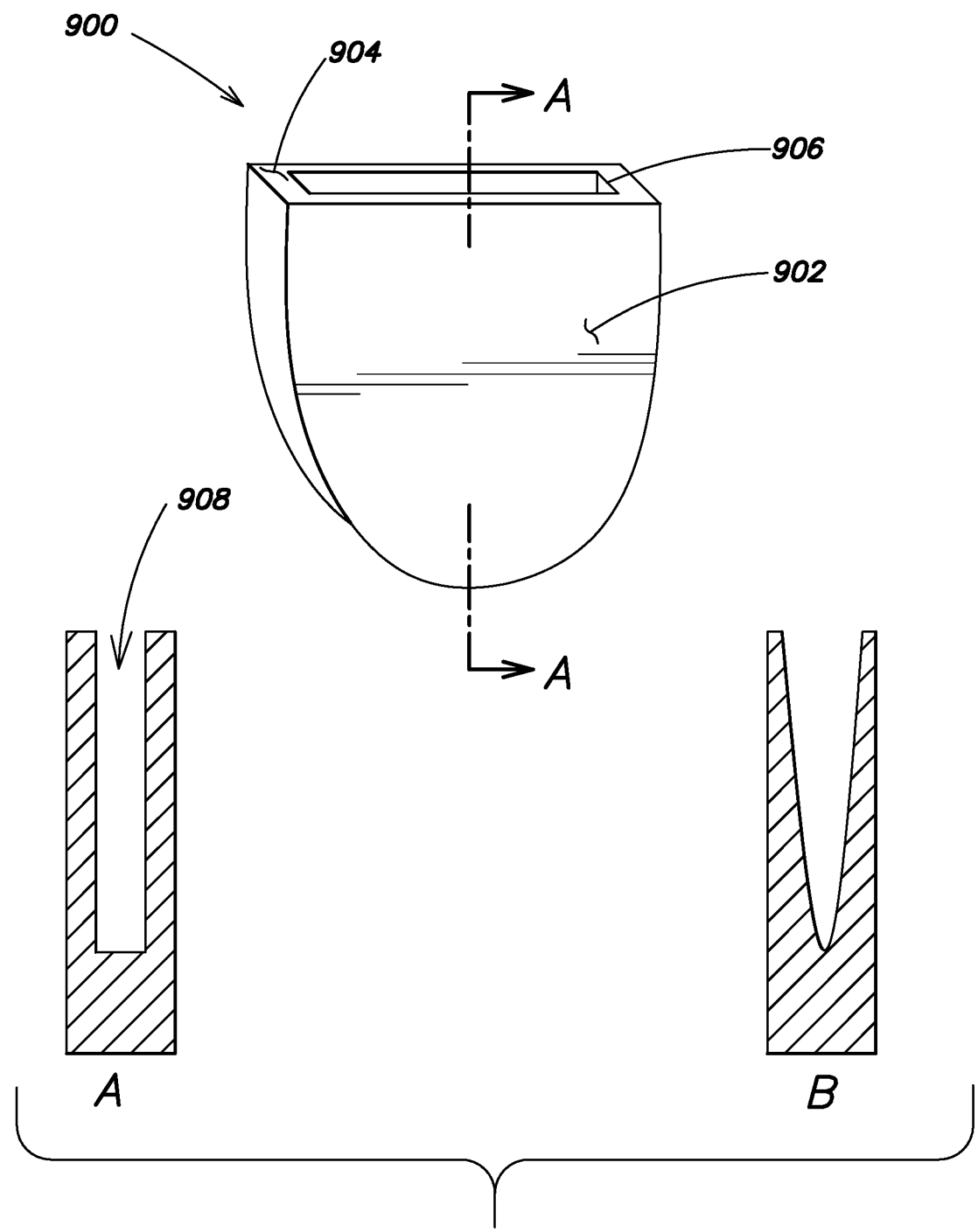
FIG. 9 is a diagram of an example embodiment of a bracket for placement on a tooth.

FIG. 9 is a diagram of an example embodiment of a bracket for placement on a tooth to which the removable component described above can be connected. Generally speaking, a bracket is formed of a rigid material forming a base, the base having a first face for attachment to a tooth, and having a second face substantially perpendicular to the first face, such as the top of the bracket. This second face has an edge defining an opening of a socket formed within the base.

In FIG. 9, a bracket 900 forms a base having a first face is shown at 902, and the second face is shown at 904, on the top of the bracket 900. The first face can be affixed to a tooth using orthodontic cement, for example. In the top of the bracket, in face 904, is an opening 906 which is configured to receive a corresponding shape, such as the projections on the removable component described above in connection with FIGS. 1-8. In this example, a cross-section along a plane shown by arrows A-A, and shown at A, illustrates a recess 908 formed in the base. The recess 908, as shown in the cross section perpendicular to the plane shown by arrows A-A, and shown at B, can have a tapered shape. For example, to mate with a tapered projection, the recess can gradually reduce in width from the face 904 to a bottom edge. The recess also can gradually reduce in thickness from the face 904 to the bottom edge. The projection can gradually reduce in both width and thickness. Such a gradual reduction can be nonuniform, and can include one or more shapes designed to provide a snapping or interlocking function.

In the foregoing embodiment, the mechanical connection of the removable component to the teeth includes projections that go into recesses in brackets attached to teeth. In another embodiment, the removable component can include recesses that go onto projections on brackets attached to teeth. Yet other designs of mechanically interlocking components can be used to provide for primary mechanical retention of the removable component to the teeth.

Also, in the foregoing embodiment, the interlocking components are illustrated as being formed on endpoints, and on the canine teeth. The primary retention components can be located anywhere along the retainer. A retainer can be configured with any size of removable component, and any number and configuration of retention components, with as few as one and as many as six components that provide primary retention. For example, intermediate teeth may use the primary retentive mechanism for additional stabilization. Yet additional components can be used to provide secondary retention and/or prosthodontic components.

Referring now to FIGS. 10-18, an alternate embodiment of projections and brackets will now be described.

Figure 10:
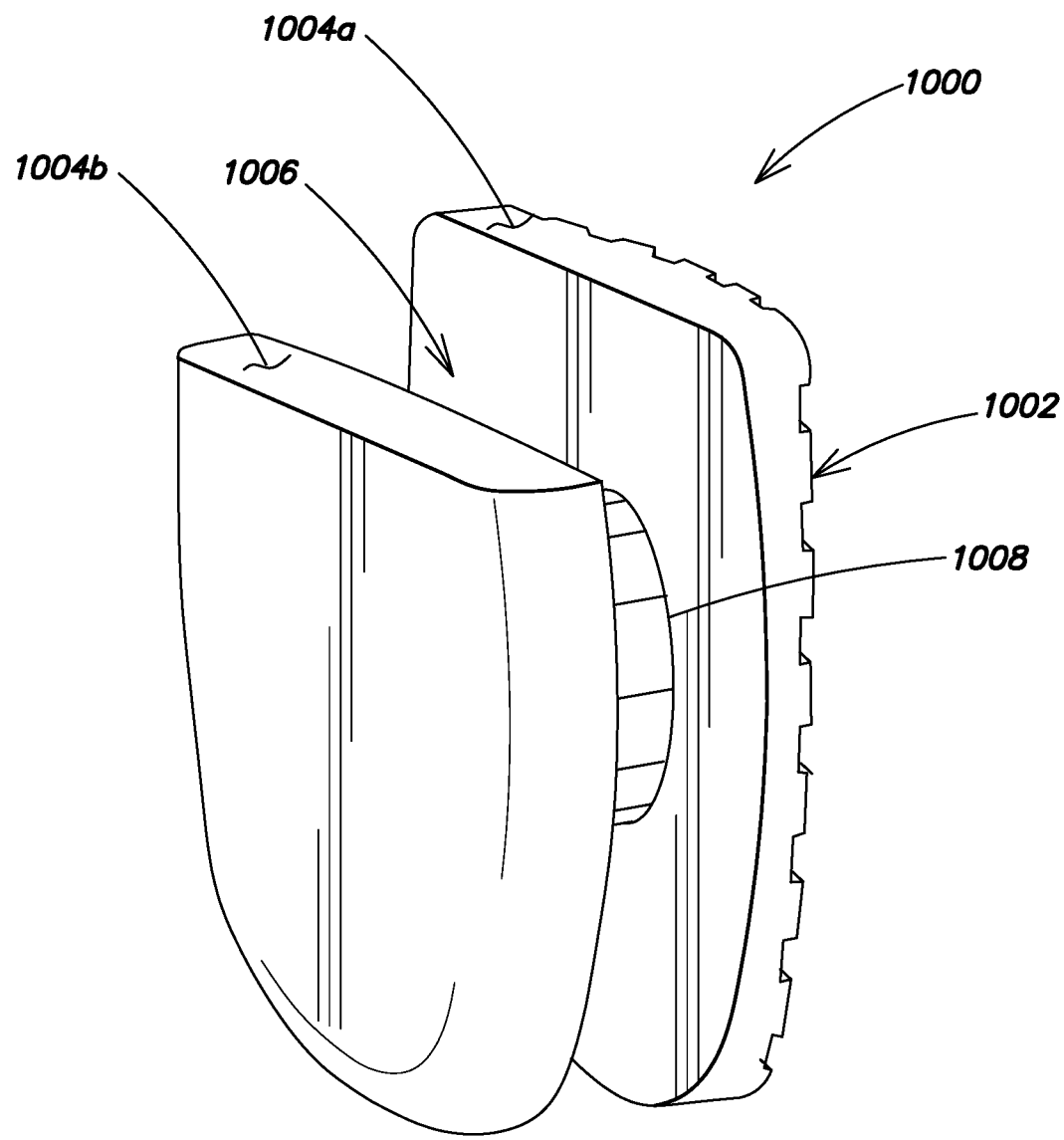
FIG. 10 is a back perspective view of a bracket in one embodiment.

In FIG. 10, a back perspective view of a bracket 1000 is shown. The bracket has a first face 1002 through which the bracket can be affixed to a tooth. The bracket 1000 has a second face, which is illustrated as formed of two separate faces 1004a and 1004b. The separate faces need not be at the same level or in the same plane, and need not be flat. The faces need not be entirely separate. In the top of this bracket, in the second face, is an opening 1006 which is configured to receive a corresponding shape from a projections formed on the removable component, an example of which is described in more detail below in connection with FIG. 11. Within the opening 1006 is a protrusion 1008 which is shown as cylindrical in shape. Other shapes can be used so long as the shape can be interlocked with a corresponding shape on a projection.

Figure 11:
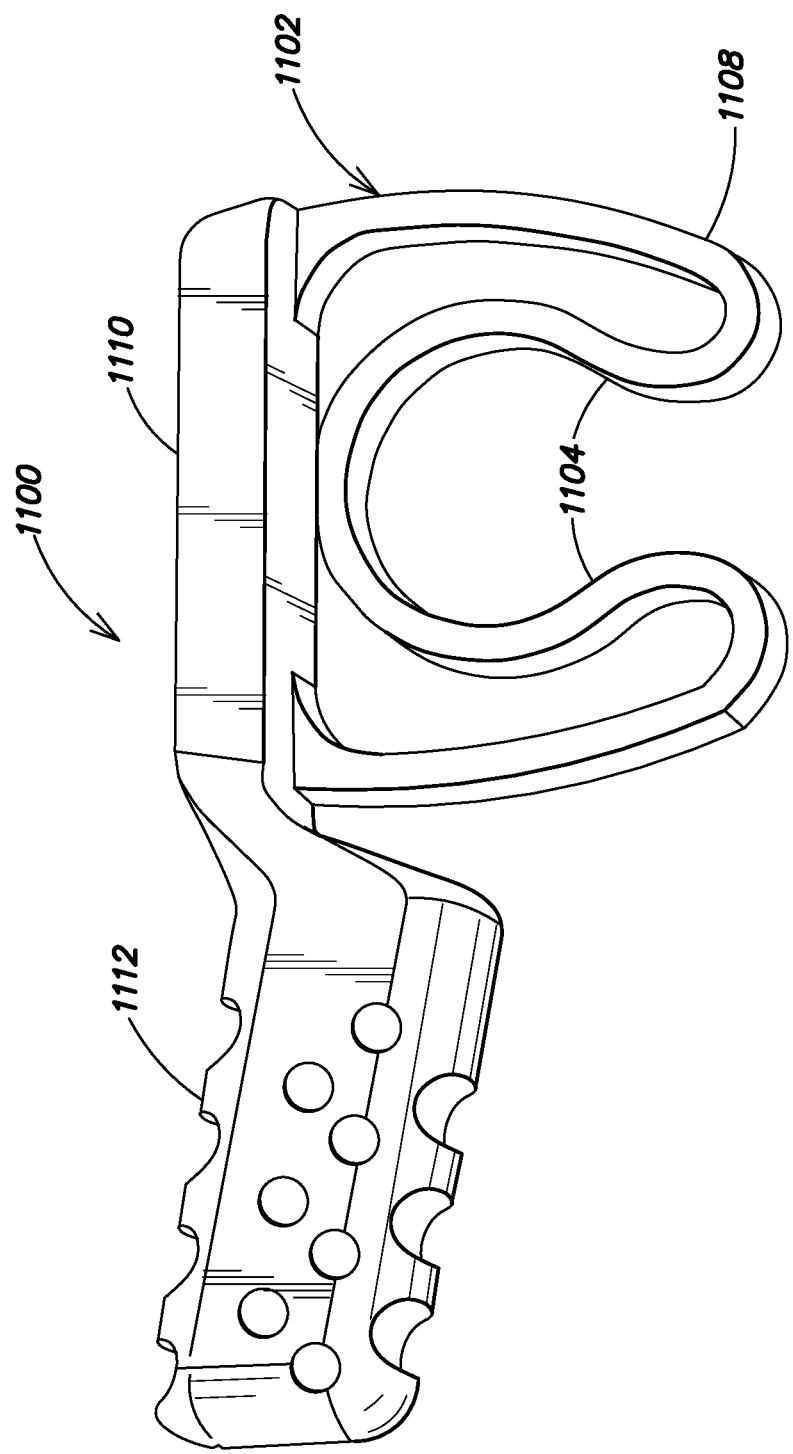
FIG. 11 is a perspective view of a projection in one embodiment.

In FIG. 11, a perspective view of a projection 1100 is shown. Such a projection has a snap-fitting member 1102 which can be inserted into the opening 1006 of the bracket 1000 in FIG. 10. The snap-fitting member 1102 includes a fitting portion 1104 having a shape that matches the protrusion 1008 on the bracket. For example, an inner diameter of the fitting portion 1104 can match the outer diameter of the protrusion 1008. The snap-fitting member can further include a flexible portion 1108 that connects the fitting portion 1104 to a top portion 1110, leaving a gap between the fitting portion 1104 and the top portion 1110. Such a structure provides a spring-like behavior to the snap-fitting member 1102.

Figure 13:
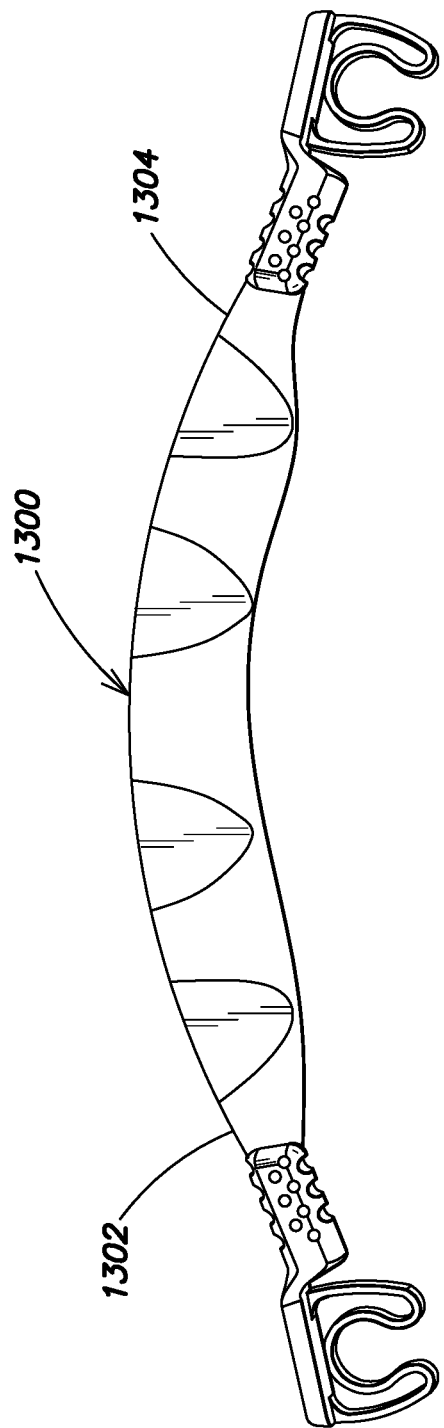
FIG. 13 is a back perspective view of a projection connected to a removable component in one embodiment.

In one embodiment, the projection 1100 includes an elongated member 1112 that can be used to mount the projection to an end of the removable component, such as shown in FIG. 13. For example is the removable component has a hollow shape, the elongated member can be configured in a shape that mates with the internal hollow shape of the removable component. There are other configurations for applying such projections to the removable component of this orthodontic retention system.

Figure 12:
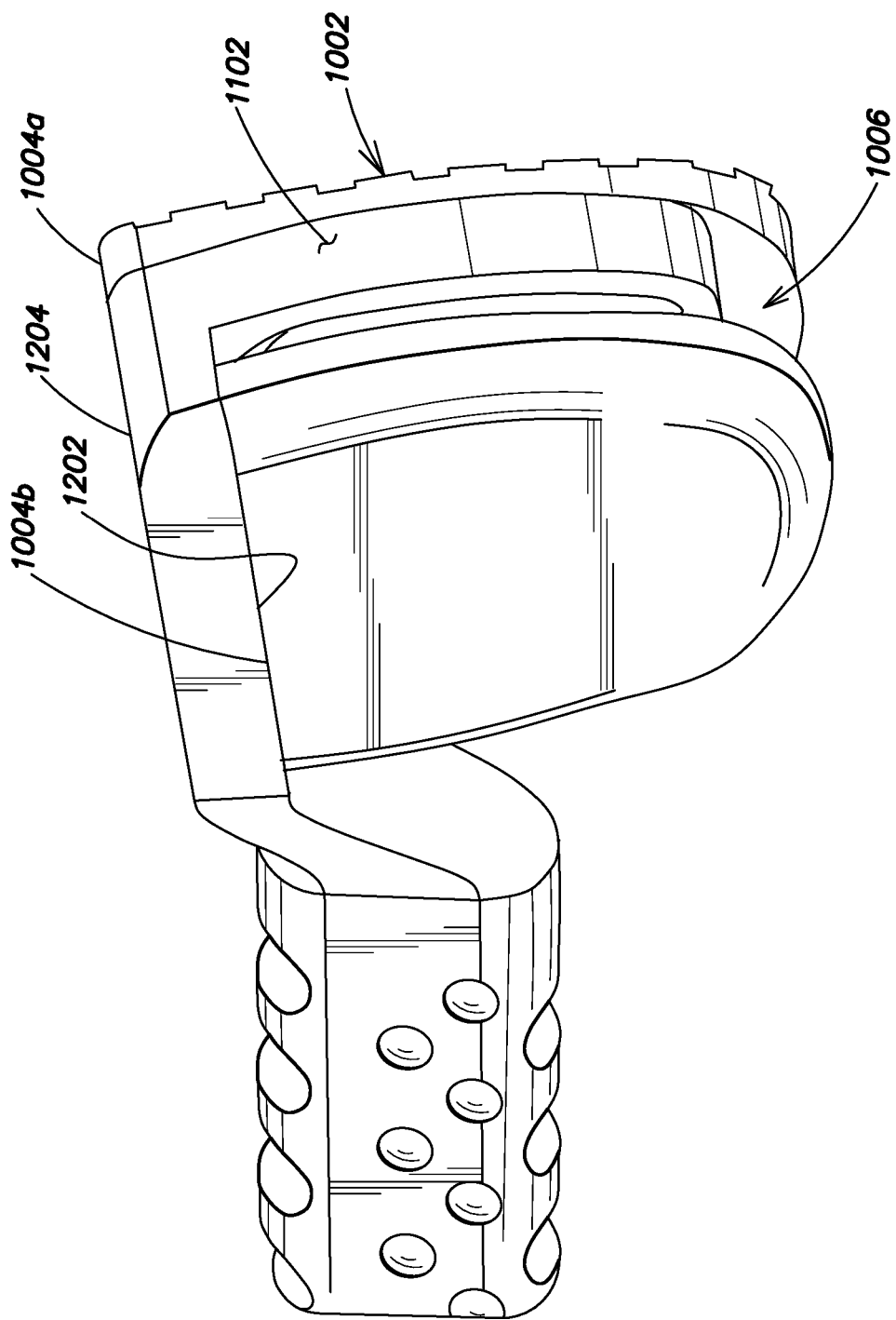
FIG. 12 is a perspective view of a projection when connected to a bracket in one embodiment.

FIG. 12 is a perspective view of the projection 1100 when connected to the bracket 1000. The snap-fitting member 1102 is shown within the opening 1006. The projection 1100 also has a face 1202 that mates with face 1004b of the bracket, and a face 1204 which, when installed, matches the face 1004a of the bracket.

In FIG. 13, such a projection (e.g., such as shown in FIG. 11) can be used on ends 1302, 1304 of a removable component 1300 to connect that removable component to endpoint teeth. The removable component can otherwise include other projections for connection to other teeth, other magnetic components and/or other replacement teeth.

Figure 14:
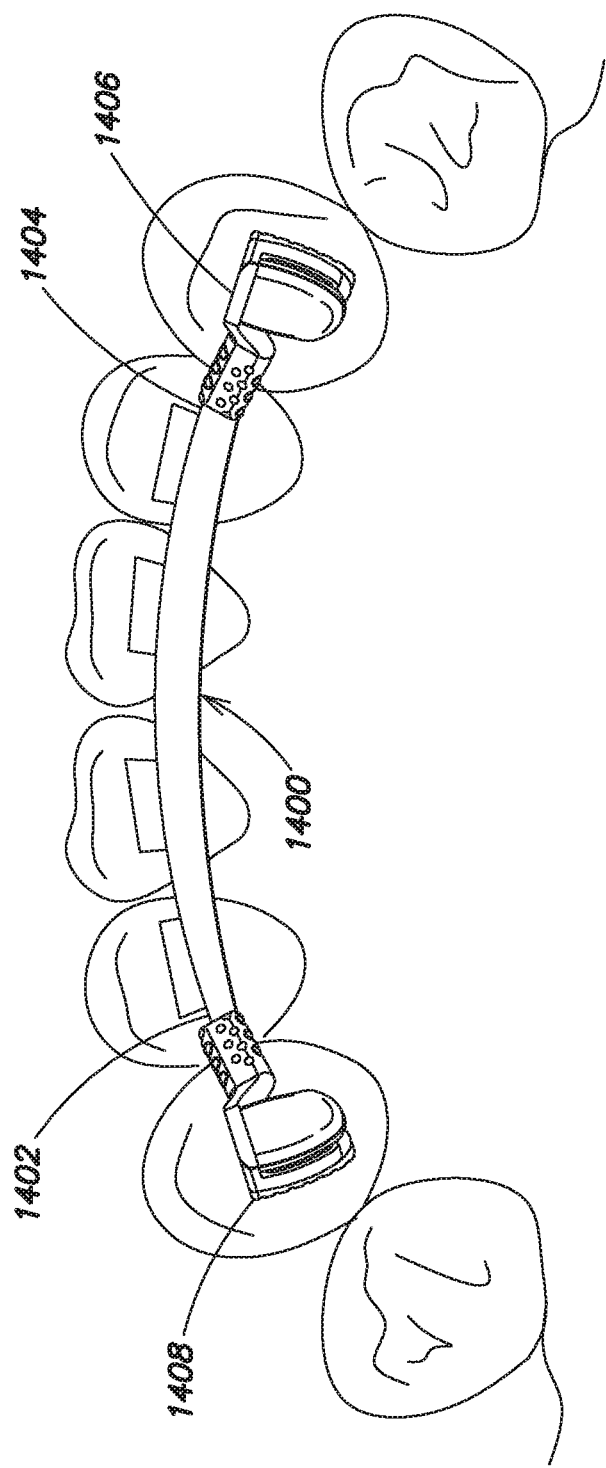
FIG. 14 is a back perspective view of a projection connected to a removable component as installed on a mandibular arch.

In FIG. 14, the projections on ends 1402, 1404 of a removable component 1400 connect that removable component to brackets 1406, 1408 (e.g., such as shown in FIG. 10) which are affixed to endpoint teeth, in this case on canine teeth on the mandibular arch. The removable component can otherwise include other projections for connection to other teeth, other magnetic components and/or other replacement teeth.

In the example retainer shown in FIGS. 13 and 14, the projections on ends 1302/1402, 1304/1404 of a removable component are illustrated as affixed to a removable component formed of acrylic configured to conform to the shape of the mandibular arch. Magnetic, or ferrometallic, components are inserted in the acrylic at positions along the acrylic corresponding to positions of the intermediate teeth, in this case the incisors. Each incisor has applied thereto a substance into which corresponding ferrometallic or magnetic materials are embedded. The magnetic interaction between the substance on the teeth and the components embedded in the acrylic assist in retaining the teeth in the desired position and orientation.

Figure 15:
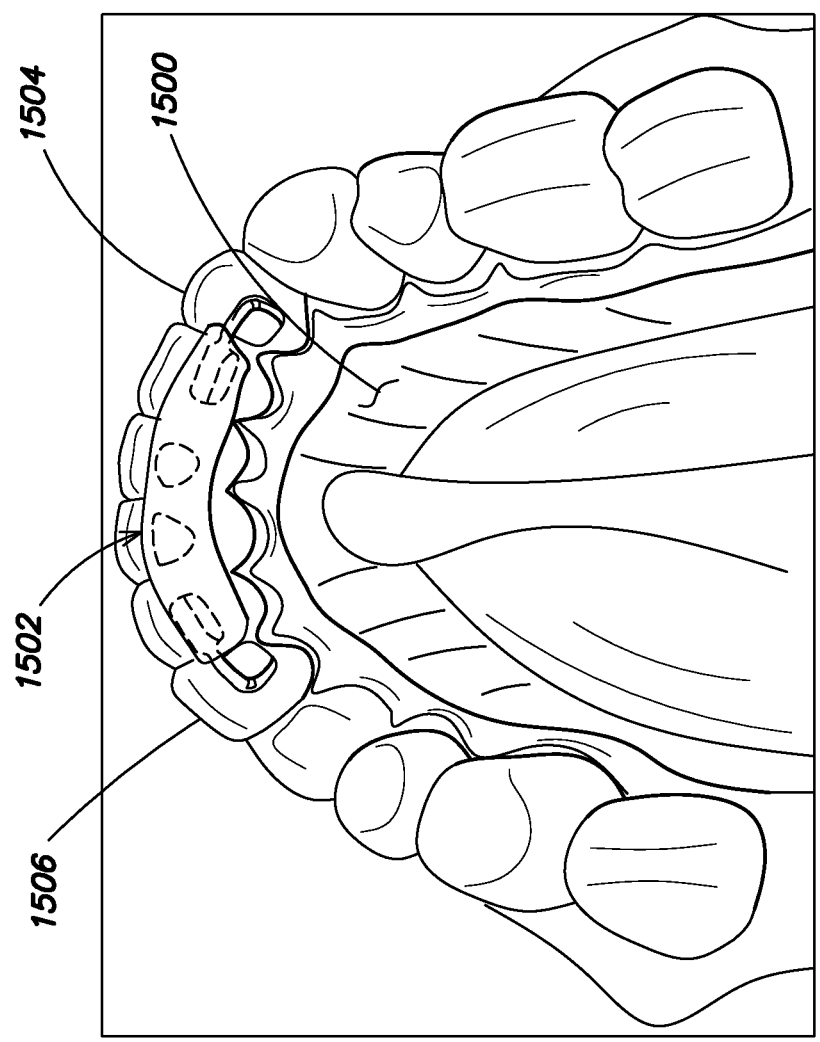
FIG. 15 illustrates are retainer installed on a model of a mandibular arch.
Figure 16:
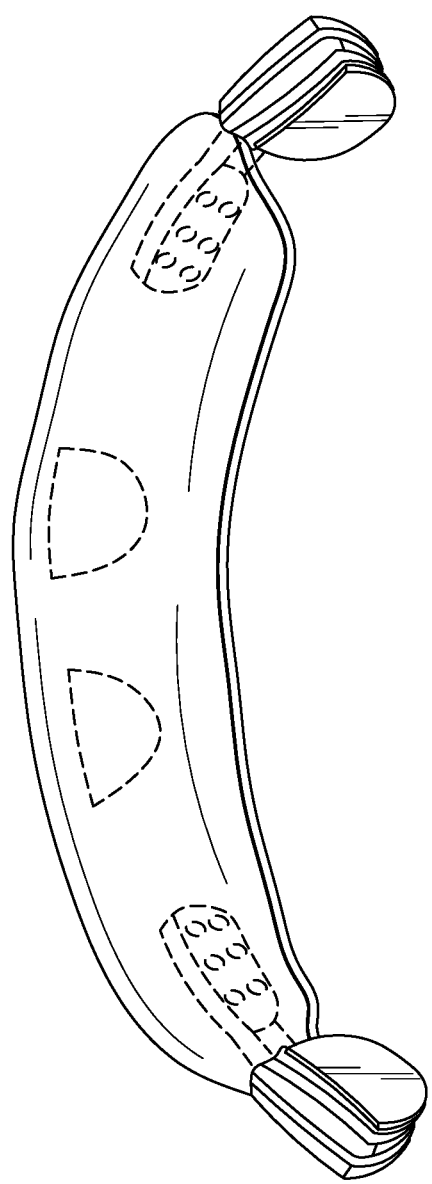
FIG. 16 illustrates a removable component attached to brackets.
Figure 17:
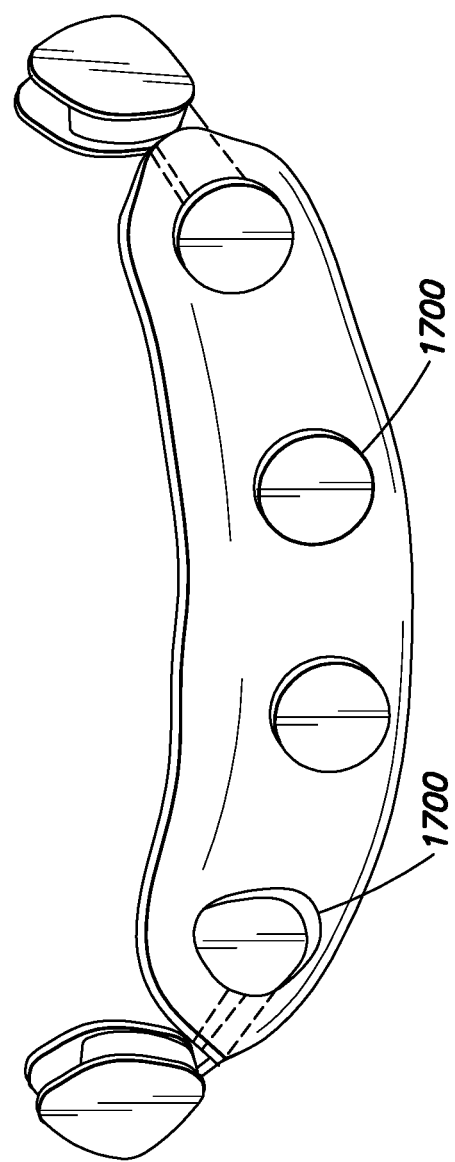
FIG. 17 is a bottom view of the removable component of FIG. 16.
Figure 18:
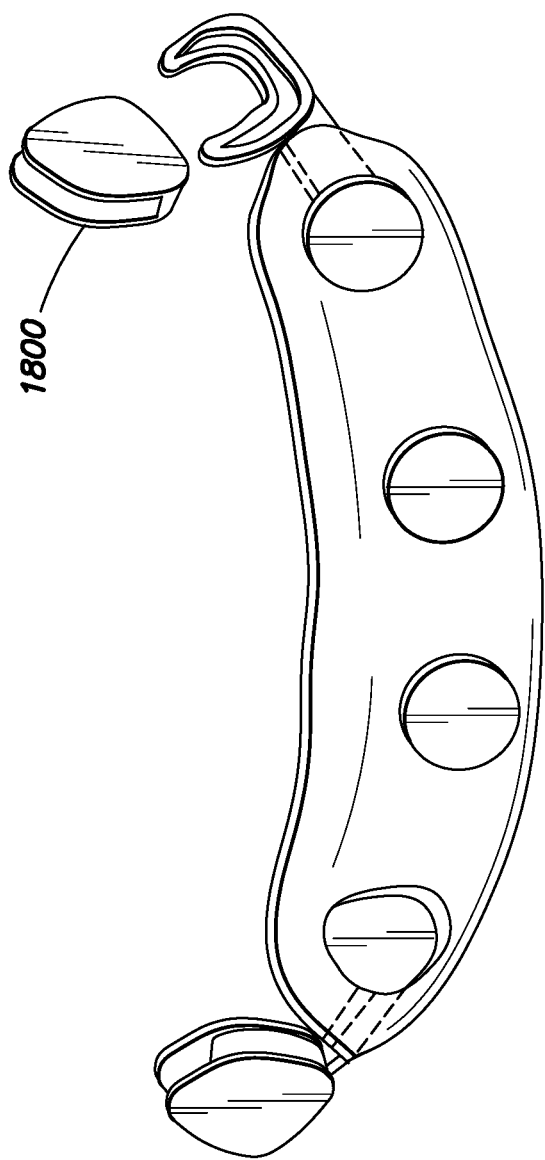
FIG. 18 illustrates the removable component separated from one of the brackets.

FIGS. 15, 16, 17 and 18 are further illustrations of a retainer such as illustrated in FIGS. 13 and 14. In FIG. 15, the retainer 1502 is illustrated as installed on a model of a mandibular arch 1500. As in FIG. 14, projections on ends of a removable component 1502 connect that removable component to brackets affixed to canine teeth 1504, 1506 on the mandibular arch. FIG. 16 illustrates the removable component, such as shown in FIG. 13 as attached to brackets, such as shown in FIG. 10. FIG. 17 is a bottom view of the removable component as shown in FIG. 16 and as attached to brackets. FIG. 17 shows the placement of magnetic or ferrometallic components, e.g., 1700, inserted in the material of the removable component at positions corresponding to intermediate teeth, in this case the incisors. FIG. 18 illustrates the removable component separated from one of the brackets 1800.

Having now described example embodiments of retainers, it should be understood that a number of different variations are possible. For example, these embodiments show a primary retention mechanism that connects the removable component to teeth is mechanical. In other embodiments, the primary retention mechanism can be magnetic or in another form. The retainer can include a primary retention mechanism of one form, e.g., mechanical, and a secondary retention mechanism, e.g., magnetic. In another embodiment a retainer can be designed to have an interlocking magnetic component as the primary retentive mechanism, or as the secondary retentive mechanism, or both.

In some applications, additional retention may be desired, or it may be desired to prevent or reduce the likelihood of patient removal of the removable component, by having a locking component. For example, the mechanical interconnection between a projection and a bracket can be designed as a snap lock.

Installation of such embodiments will now be described in more detail.

A medical or dental provider trained in the field generally would perform the initial insertion of the removable fixed retainer. The provider measures the distance between the endpoint teeth, such as the canine teeth on the mandibular arch. Such a measurement can be made on a model of the patient's mouth or intra-orally. The adjustable, removable component is expanded or reduced, as the case may be, to an appropriate size and is locked in the position providing the desired length.

In the example above with a further sliding component with projections for intermediate teeth, this sliding component is then shifted to adapt to the anterior incisor region lining up the remaining three incisors. After the proper dimension and plane is found and adapted to the incisors, this sliding component is locked in place.

Fixed components, i.e., brackets, are affixed to the endpoint teeth (such as the canine teeth on the mandibular arch). The brackets can be attached to the removable component.

The provider can then use either a direct bond or indirect bond technique to adhere the brackets to the teeth, particularly ensuring proper affixation of the brackets against the lingual surface of the endpoint teeth.

In the direct technique, the provider isolates and cleans the teeth to be bonded with a phosphoric acid for a period of time ranging from 30-40 seconds removing all saliva contaminants. A primer/adhesive is then placed on the tooth and "bracket" part of the canine. The provider then allows proper set time depending on bonding materials selected.

After bonding is set, the removable/fixed retainer can then be removed vertically, for example using a tool. Re-insertion also can be tested. Magnetic brackets can then be affixed as well. Such brackets can be bonded via direct technique as explained above for individual brackets. Alternatively, the magnetic or ferrometallic materials can reside in a material that is "painted" on the teeth. In the case where teeth need to be replaced, an attachment bracket can be added to the removable component. The removable "bracket" can be restored with dental material.

Figure 19:
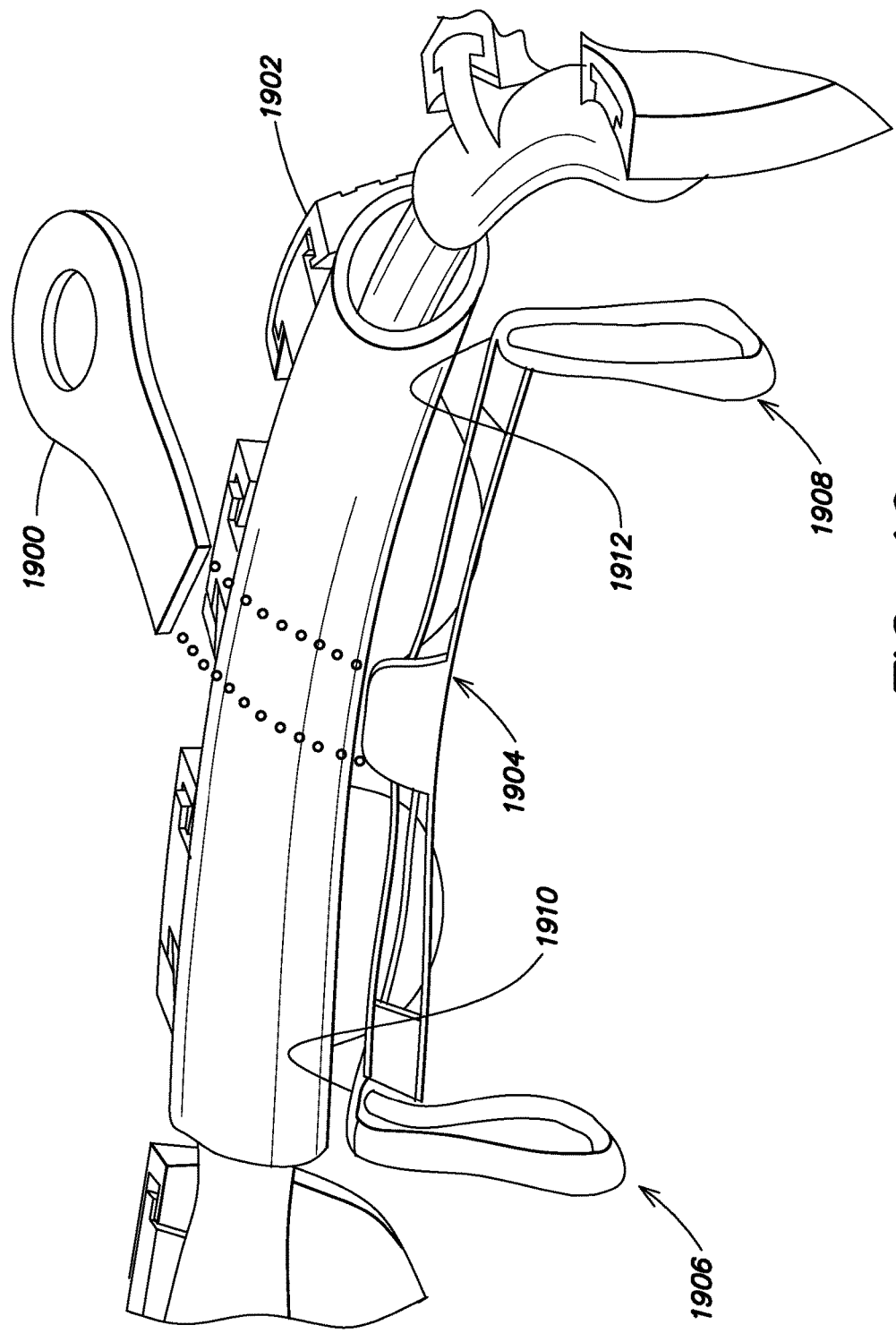
FIG. 19 is an illustration of an insertion/removal tool.

An insertion and removal tool can be provided as a handheld device having a handle, such as in the shape and size of a typical handheld disposable shaver or toothbrush with a grip, and an arm supporting a tip and which locks into the handle. The tool is manipulated by a provider or a patient so as to cause the tip to pull or push the removable component vertically with respect to its primary retention component(s) to either insert or remove the removable component. An example of such a tool is shown in FIG. 19. A handle 1900 is shown, with dashed lines to shown the removable component 1902 behind it. An arm 1904 extends the length of one of the sections of the removable component, as indicated between a first end 1906 and a second end 1908. In this embodiment, tips 1910 and 1912 can be used to pull up on the removable component 1902. Ends 1906 and 1908 and be used to push down on the removable component.

The foregoing embodiments allow the removable component to be inserted and removed in a vertical motion, which reduces a likelihood that the removable component will accidentally come dislodged during eating or other normal uses. Such removal can allow for a patient to more easily perform various dental hygiene tasks, such as brushing, flossing and otherwise cleaning of the teeth, mouth and retainer.

An orthodontic retention system can be provided in a form of a kit with a removable component, brackets for endpoint teeth and other parts for attachment to intermediate teeth. One or more insertion or removal tools can also be provided in the kit to be given to the patient. The kit can also include installation and/or use instructions. A kit can include any one or more of the following: adjunctive bracket for anterior/posterior teeth with slot for attaching orthodontic wires; adjunctive bracket for anterior/posterior teeth with varying shape depending on tooth anatomy; adjunctive bracket for anterior/posterior teeth with magnetic properties; adjunctive restorative replacement parts for missing anterior/posterior teeth that attached to extension arm of removable fixed retainer; replacement parts of main body of removable fixed retainer.

Manufacturing of such components as described herein can be performed using a variety of different techniques. For some components, particularly brackets and/or removable or adjustable components, an additive manufacturing process, commonly referred to a three-dimensional (3D) printing, can be used. Materials that can be used for such components include ceramics, metals such as stainless steel, titanium, cobalt chromium and wironium, or such as dental acrylic, bondable reinforcement ribbon such as RIBBOND brand ribbons, curable resins such as TRIAD brand provisional material, and polymer composite technologies such as those used in SIMPLICLEAR brand orthodontic materials, and other materials commonly used in orthodontic applications. Different components of the retention system can be made of different materials.

Some embodiments include a combination of components of different materials. Such a retention system can be manufactured using two different types of additive manufacturing equipment (e.g., different types of 3D printers). Metal parts, such as the brackets and projections of the primary retentive components of the retainer, can be manufactured using a first printer for the type of material used for these components. Next, these parts are oriented on a model (e.g., a model of the teeth for the patient that is receiving the retainer), and the model is placed into a second printer for the type of material for the other components. The model is placed in the printing area of second printer in an orientation that matches where additional components will be manufactured. A digital model of the model may be used by the printer to assist in this orientation. The other components are then manufactured in the environment of the model in the second printer. Such a manufacturing process, of preparing one component using an additive manufacturing process of one type, placing the component on a model, and then manufacturing a second component using an additive manufacturing process of a second type, can be applied to other intraoral devices, other medical devices and other nonmedical devices.

In some embodiments, some components such as the primary retentive components can be manufactured and then applied to the teeth. Other components, such as an acrylic component interconnecting the primary retentive components, can be shaped and cured intraorally. Such an installation provides a custom fit for each patient.

Accordingly, in one aspect, an adjustable orthodontic retainer, comprises a first fixed component of a material forming a base, the base having a first face for attachment to a tooth, and having a second face having an edge defining an opening for a socket formed within the base. The retainer further comprises a second fixed component of a material forming a base, the base having a first face for attachment to a tooth, and having a second face having an edge defining an opening for a socket formed within the base. The retainer further comprises an adjustable component comprising a first projection and a second projection, the first projection having a shape that mates with the socket of the first fixed component, the second projection having a shape that mates with the socket of the second fixed component, the component having a curved member with an adjustable length between the first projection and the second projection.

In another aspect, a blended convertible orthodontic retainer, comprises a first fixed component of a rigid material forming a base, the base having a first face for attachment to a tooth, and having a second face substantially perpendicular to the first face, the second face having an edge defining an opening of a socket formed within the base. The retainer further comprises a second fixed component of a rigid material forming a base, the base having a first face for fixed attachment to a tooth, and having a second face substantially perpendicular to the first face, the second face having an edge defining an opening of a socket formed within the base. The retainer further comprises a removable component comprising a first projection and a second projection, the first projection having a shape that removably mates with the socket of the first fixed component, the second projection having a shape that removably mates with the socket of the second fixed component.

In another aspects, a blended magnetic orthodontic retainer, comprises a first fixed component of a material forming a base, the base having a first face for attachment to a tooth, and having a second face having an edge defining an opening of a socket formed within the base. The retainer further comprises a second fixed component of a material forming a base, the base having a first face for attachment to a tooth, and having a second face having an edge defining an opening of a socket formed within the base. The retainer further comprises a base formed of a material, the base being configured to be applied to a back face of a tooth, and having a face opposite the back face of the tooth and forming a surface, the material including at least one of a magnetic material or ferrometallic material. The retainer further comprises a component comprising a first projection and a second projection, the first projection having a shape that mates with the socket of the first fixed component, the second projection having a shape that mates with the socket of the second fixed component, and a third projection having a surface that mates with the surface of the base, wherein the third projection includes at least one of a magnetic material or ferrometallic material such that magnetic attraction occurs between the third projection and the base.

In another aspect, a blended orthodontic retainer, comprises a first fixed component of a material forming a base, the base having a first face for attachment to a tooth, and having a second face having an edge defining an opening of a socket formed within the base. The retainer further comprises a second fixed component of a material forming a base, the base having a first face for attachment to a tooth, and having a second face having an edge defining an opening of a socket formed within the base. The retainer further comprises a component comprising a first projection and a second projection, the first projection having a shape that mates with the socket of the first fixed component, the second projection having a shape that mates with the socket of the second fixed component, and a third element spaced between the first and second projections and having a shape of a tooth that fits between teeth when the component is attached to the first and second brackets.

In another aspect, a kit for providing a blended convertible orthodontic retainer, comprises a first fixed component of a rigid material forming a base, the base having a first face for attachment to a tooth, and having a second face substantially perpendicular to the first face, the second face having an edge defining an opening of a socket formed within the base. The kit further comprises a second fixed component of a rigid material forming a base, the base having a first face for attachment to a tooth, and having a second face substantially perpendicular to the first face, the second face having an edge defining an opening of a socket formed within the base. The kit further comprises a removable component comprising a first projection and a second projection, the first projection having a shape that removably mates with the socket of the first fixed component, the second projection having a shape that removably mates with the socket of the second fixed component.

In another aspect, an orthodontic bracket, for an orthodontic retainer, comprises a rigid material forming a base, the base having a first face for attachment to a tooth, and having a second face substantially perpendicular to the first face, the second face having an edge defining an opening of a socket formed within the base.

In another aspect, an adjustable component for an orthodontic retention system, for a blended convertible orthodontic retainer, comprises a first projection and a second projection, the first projection having a shape that mates with a socket of a first fixed component, the second projection having a shape that mates with a socket of a second fixed component, the component having a curved member with an adjustable length between the first projection and the second projection.

In another aspect, a removable component for an orthodontic retention system, for a blended convertible orthodontic retainer, comprises a first projection and a second projection, the first projection having a shape that removably mates with a socket of a first fixed component, the second projection having a shape that removably mates with a socket of a second fixed component. The removable component also can be adjustable by having a curved member with an adjustable length between the first projection and the second projection.

Another aspect is a bracket used in the any of the foregoing aspects.

Another aspect is a component that mates with brackets as in any of the foregoing aspects.

Another aspect is the insertion or removal tool as described herein.

Another aspect is the a manufacturing process, of preparing one component using an additive manufacturing process of one type, placing the component on a model, and then manufacturing a second component using an additive manufacturing process of a second type. This aspect can be applied to manufacture components of any of the foregoing aspects, as well as for other intraoral devices, other medical devices and other nonmedical devices.

In any of the foregoing aspects, the removable component comprises an adjustable component comprising a curved member with an adjustable length between the first projection and the second projection.

In another aspect, a kit for providing the retainer of any of the foregoing aspects comprises a plurality of brackets, of any of the foregoing aspects, and the adjustable or removable component, of any of the foregoing aspects, that mates with the bracket.

In any of the foregoing aspects, the orthodontic retainer can be an adjustable orthodontic retainer, a blended convertible orthodontic retainer, or a blended orthodontic retainer, a blended magnetic orthodontic retainer.

It should be understood that the subject matter defined in the appended claims is not limited to the specific implementations described above. The specific implementations described above are disclosed by way of example only.

What is claimed is:

1. A kit for providing an orthodontic retainer, comprising:
a first fixed component of a rigid material forming a base, the base having a first face for attachment to a first tooth, and having a second face substantially perpendicular to the first face, the second face having an edge defining an opening of a socket formed within the base;
a second fixed component of a rigid material forming a base, the base having a first face for attachment to a second tooth, and having a second face substantially perpendicular to the first face, the second face having an edge defining an opening of a socket formed within the base;
a third component comprising a curved member having a length and curvature to match an arch formed along teeth between the first tooth and the second tooth, the curved member further supporting a first projection and a second projection, the first projection having a shape and position along the curved member that mates with the socket of the first fixed component, the second projection having a shape and position along the curved member that mates with the socket of the second fixed component; and an intermediate component having a shape and adapted to be placed on the curved member at a position along the curved member for retention of at least a third tooth from among the teeth between the first tooth and the second tooth, wherein the intermediate component comprises an element formed on the curved member and having a surface that mates with material on the third tooth, wherein the element comprises at least one of a magnetic material or ferrometallic material, and wherein the material on the third tooth comprises at least one of a magnetic material or ferrometallic material such that magnetic attraction occurs between the element and the material on the third tooth;

wherein the kit further comprises the material for application to the surface of the third tooth; and wherein the material for the third tooth comprises a biocompatible coating that can be applied to a tooth surface and in which biocompatible particles of magnetic or ferrometallic material are embedded.

2. The kit of claim 1, wherein the curved member comprises acrylic configured to conform to a shape of an arch along teeth between the first tooth and the second tooth, and wherein the element comprises a component inserted in the acrylic at a position corresponding to the third tooth.

3. The kit of claim 1, wherein the third component is a removable component, wherein the shape of the first projection removably mates with the socket of the first fixed component, and the shape of the second projection removably mates with the socket of the second fixed component.

4. An orthodontic retainer, comprising:

a first fixed component of a rigid material forming a base, the base having a first face attached to a first tooth, and having a second face substantially perpendicular to the first face, the second face having an edge defining an opening of a socket formed within the base;

a second fixed component of a rigid material forming a base, the base having a first face attached to a second tooth, and having a second face substantially perpendicular to the first face, the second face having an edge defining an opening of a socket formed within the base;

a third component comprising a curved member having a length and curvature to match an arch formed along teeth between the first tooth and the second tooth, the curved member further supporting a first projection and a second projection, the first projection having a shape and position along the curved member that mates with the socket of the first fixed component, the second projection having a shape and position along the curved member that mates with the socket of the second fixed component; and an intermediate component having a shape and formed on the curved member at a position along the curved member for retention of at least a third tooth from among the teeth between the first tooth and the second tooth, wherein the intermediate component comprises an element formed on the curved member and having a surface that mates with material on the third tooth, wherein the element comprises at least one of a magnetic material or ferrometallic material, and wherein the material on the third tooth comprises at least one of a magnetic material or ferrometallic material such that magnetic attraction occurs between the element and the material on the third tooth; and wherein the material on the third tooth comprises a biocompatible coating that can be applied to a tooth surface and in which biocompatible particles of magnetic or ferrometallic material are embedded.

5. The orthodontic retainer of claim 4, wherein the curved member comprises acrylic configured to conform to a shape of an arch along teeth between the first tooth and the second tooth, and wherein the element comprises a component inserted in the acrylic at a position corresponding to the third tooth.

6. The orthodontic retainer of claim 4, wherein the third component is a removable component, wherein the shape of the first projection removably mates with the socket of the first fixed component, and the shape of the second projection removably mates with the socket of the second fixed component.

* * * * *